United States Patent [19]
Harada et al.

[11] Patent Number: 6,150,545
[45] Date of Patent: Nov. 21, 2000

[54] METAL ACETYLIDE COMPOUND AND PROCESS FOR PREPARING THE SAME

[75] Inventors: Akio Harada; Yoshiki Okamoto, both of Osaka, Japan

[73] Assignee: Daiken Chemical Co., Ltd., Osaka, Japan

[21] Appl. No.: 09/308,801

[22] PCT Filed: Sep. 21, 1998

[86] PCT No.: PCT/JP98/04267

§ 371 Date: May 24, 1999

§ 102(e) Date: May 24, 1999

[87] PCT Pub. No.: WO99/16773

PCT Pub. Date: Apr. 8, 1999

[30] Foreign Application Priority Data

Sep. 30, 1997 [JP] Japan .................................. 9-303275

[51] Int. Cl.[7] .............................. C07F 1/00; C07F 15/00
[52] U.S. Cl. .......................................... 556/112; 556/136
[58] Field of Search ..................................... 556/112, 136

[56] References Cited

U.S. PATENT DOCUMENTS

| | | | |
|---|---|---|---|
| 3,800,030 | 3/1974 | Long | 423/491 |
| 4,835,272 | 5/1989 | Sato et al. | 544/158 |

OTHER PUBLICATIONS

Author: The American Chemical Society Title: "Chemical Abstract", Abstract. No. 91946h Date: Oct. 15, 1973 Pertinent Page: 416.

Author: Allan T. Casey and Angelica M. Vecchio Title: "The electrochemical synthesis of metallocenes, polymethylmetallocenes, open metallocenes and metal phenylacetylides" Date: 1990 Pertinent Pages: 513–522.

*Primary Examiner*—Porfirio Nazario-Gonzalez
*Attorney, Agent, or Firm*—Koda & Androlia

[57] ABSTRACT

The present invention relates to novel compounds which contain no sulfur or chlorine, and which thus contribute to the cleaning of the environment as organo-metal complexes used in metal pastes, etc., and a method for manufacturing the same.

Metal acetylide compounds expressed by the general formula $M(-C{\equiv}C-R)_n$ (in the formula, M indicates a metal atom, n indicates the valence number of the metal atom M, and R indicates a hydrocarbon group with 1 to 8 carbon atoms which may or may not contain an oxygen atom) are provided as novel organo-metal complexes. Since these compounds contain no sulfur or chlorine, there is no release of sulfurous acid gas or chlorine compounds when the compounds are used in metal pastes, etc., even if the pastes are fired. Accordingly, these compounds contribute to the cleaning of the environment.

In the present invention, solid sulfites are used as metal reducing agents; accordingly, simple stoichiometric control of the reaction is possible, so that metal acetylide compounds can easily be obtained. Furthermore, since no sulfurous acid gas is generated in this manufacturing method, there are no concerns about environmental pollution, and the method contributes to the cleaning of the environment.

6 Claims, No Drawings

METAL ACETYLIDE COMPOUND AND PROCESS FOR PREPARING THE SAME

TECHNICAL FIELD

The present invention relates to novel chemical substances constituting organo-metal complexes which reduce and deposit metals by firing, and more particulary to metal acetylide compounds which contain no sulfur or chlorine and are therefore clean with respect to the environment by not emitting environmental contaminants such as sulfurous acid gas or chlorine compounds, etc. during manufacturing and firing and further to a method for manufacturing such compounds.

BACKGROUND TECHNOLOGY

Ordinarily, in cases where electrodes are formed on insulating substrates or semiconductors, a method is used in which: a metal paste containing an organo-metal complex of gold or platinum, etc. is prepared; this metal paste is applied as a coating in a prescribed pattern; and the pattern is fired so that the organic component is scattered, thus causing reductive deposition of the metal so that metal electrodes of the pattern are formed. Fields in which organo-metal complexes are used are not limited to this semiconductor industry; such complexes are currently widely used in a variety of fields such as electronic devices, ceramics and art, etc.

Conventionally, such organo-metal complexes include, for example, terepineolrhodium sulfide ($C_{10}H_{18}SRhCl_x$), terepineolplatinum sulfide ($C_{10}H_{18}SPtCl_x$) and terepineolpalladium sulfide ($C_{10}H_{18}SPdCl_x$), etc. These compounds are also known by the abbreviated names of rhodium balsam, platinum balsam and palladium balsam. In addition, precious metal balsams such as gold balsam and ruthenium balsam, etc. are also known.

Methods in which a terpene type compound is reacted with sulfur to produce a terpene type balsam, after which an organo-metal complex is manufactured by reacting hexachlororhodium ($H_3RhCl_6$), hexachloroplatinum ($H_2PtCl_6$) or hexachloropalladium ($H_2PdCl_6$) with this terpene type balsam, are known as methods for manufacturing such organo-metal complexes.

Such conventional organo-metal complexes involve problems. First of all, recent environmental problems, especially problems of atmospheric contamination, have been caused by $NO_x$ and $SO_x$, and chlorine compounds are not an exception in this regard. In order to protect the environment in plants and areas where such gases are handled, the installation of desulfurizing equipment has become a must. Since sulfur is used in the manufacturing stage of the organo-metal complexes, there is a danger that $SO_2$ gas will be generated. Furthermore, organic matter is decomposed in the firing stage in which such complexes are used in the form of a metal paste, so that $SO_2$ gas and chlorine compounds, etc. are discharged. Accordingly, extensive equipment is required in order to maintain a clean environment, and the complete avoidance of gas leakage accidents has been difficult. Another problem is that residual impurities such as sulfides and chlorine compounds tend to remain on the surfaces of physical objects after firing.

Secondly, in the manufacturing process, sulfur is injected into terpene type compounds (which are organic solvents), and terpene type balsams are gradually produced while the mixture is heated for a long period of time, i. e., 20 to 30 hours. Accordingly, the difficulty of controlling chemical reactions in the solvent over a long period of time has also been encountered.

DISCLOSURE OF THE INVENTION

The present invention was devised in order to overcome the above-described drawbacks. More specifically, the present invention proposes novel organo-metal complexes comprising three to four elements which contain a metal, carbon, hydrogen and in some cases oxygen, i.e., organo-metal complexes which do not contain sulfur or chlorine that are harmful to the environment.

The novel organo-metal complexes of the present invention are metal acetylide compounds which can be expressed by the general formula M(—C≡C—R)$_n$ (in this formula, M indicates a metal atom, n indicates the valence number of the metal atom M, and R indicates a hydrocarbon group with 1 to 8 carbon atoms which may or may not contain an oxygen atom). Furthermore, metal acetylide compounds are proposed in which M is a precious metal atom, and R is an aliphatic hydrocarbon group which contains oxygen in the form of a hydroxy group in cases where oxygen is contained in this hydrocarbon group. Moreover, metal acetylide compounds are proposed in which M is a precious metal atom, and R is a hydrocarbon group containing at least a cyclic hydrocarbon which contains oxygen in the form of a hydroxy group in cases where oxygen is contained in the above-described hydrocarbon group.

A method for manufacturing metal acetylide compounds is also proposed in which a metal salt and an acetylene derivative expressed by the formula H—C≡C—R (R indicates a hydrocarbon group with 1 to 8 carbon atoms which may or may not contain an oxygen atom) are reacted so that the metal atom of the metal salt is exchanged with the hydrogen atom of the acetylene derivative, thus producing a metal acetylide compound expressed by the formula M(—C≡C—R)$_n$ (here, M indicates a metal atom, and n is the valence number of such a metal atom).

Furthermore, a method for manufacturing metal acetylide compounds is proposed in which a sulfite is added to a metal salt so that the metal atom of the metal salt is reduced, the acetylene derivative is introduced thereinto, and the reduced metal atom and the hydrogen atom of the acetylene derivative are exchanged so that a metal acetylide compound is produced.

In addition, a method for manufacturing metal acetylide compounds is proposed in which an exchange-promoting substance is added in order to cause the exchange of the above-described metal atom or reduced metal atom with the hydrogen atom of the above-described acetylene derivative in the methods described above. Furthermore, a method for manufacturing metal acetylide compounds is proposed in which the reaction is promoted by preparing a mixed solvent comprising water and a hydrophilic organic solvent, dissolving the metal salt and sulfite in the aqueous component of the mixed solvent, and dissolving the acetylene derivative in the hydrophilic organic solvent contained in the mixed solvent.

The present inventors conducted diligent research in order to develop novel organo-metal complexes which contain no sulfur or chlorine that causes environmental contamination, and which can be manufactured without using sulfur in the manufacturing process. As a result of this research, the inventors discovered that metal acetylide compounds, which are a type of acetylene derivative, are suited to this purpose. The present invention was based on this discovery.

More specifically, the novel organo-metal complexes of the present invention are expressed by the general formula M(—C≡C—R)$_n$. In this general formula, M indicates a metal atom; and this metal atom includes, for example, any of a wide range of metallic elements such as Bi, Cu, In, Ni, Ru, Rh, Pd, Ag, Os, Ir, Pt, Au, etc. However, precious metals which have a high stability as metal pastes, such as a silver paste or gold paste, etc., are utilized. Here, the term "precious metals" refers to Au, Ag and metallic elements belonging to the platinum family (Ru, Rh, Pd, Os, Ir and Pt).

n indicates the valence number of the metal atom M; thus, for example, Au has monovalent and trivalent forms, Ag has monovalent and divalent forms, and Pt has divalent, tetravalent and hexavalent forms, etc. In other words, not only does this value vary according to the type of metal involved, but specified metallic elements may have a plurality of valence numbers. In the present invention, as will be described later, there are cases in which metal acetylide compounds are produced without reducing metal acids such as chloroauric acid, etc., or metal acid salts such as potassium chloroaurate, etc., and cases in which metal acetylide compounds are produced by reducing the metals. Accordingly, the question of whether the valence number of the metal involved remains unchanged or drops depends on the individual reaction involved.

The novel chemical substances of the present invention are obtained utilizing acetylene which has active hydrogen. In other words, the ligand —C≡C—R has an acetylene bond; and the hydrogen atom bonded to the triple-bonded carbon atom has the property of being extremely easily moved and is referred to as "active hydrogen". The present inventors selected metal acetylide compounds as organometal complexes in order to allow positive utilization of this property whereby active hydrogen is easily exchanged with metal atoms. In other words, the object of the present invention is to produce metal acetylide compounds expressed by the formula M(—C≡C—R)n by reacting metals with acetylene derivatives expressed by the formula H—C≡C—R. In particular, the selection of a hydrocarbon group R which contains no harmful sulfur or chlorine prevents sulfides and chlorine compounds from being produced, so that novel metal acetylide compounds which contribute to a cleaning of the environment can be obtained.

In the present invention, R in the above-described ligand —C≡C—R is a hydrocarbon group with 1 to 8 carbon atoms which may or may not contain an oxygen atom. Accordingly, the number of carbon atoms in the ligand as a whole is 3 to 10. In cases where the number of carbon atoms in the ligand is less than 3, the ligand does not readily dissolve in solvents; at the same time, the explosive properties of the ligand are increased so that handling becomes difficult. On the other hand, in cases where the number of carbon atoms in the ligand exceeds 10, the amount of metal in the substance becomes relatively small, so that a metal film cannot be formed when this substance is formed into a paste. In other words, in cases where the metal acetylide compounds of the present invention are utilized in metal pastes, etc., it is necessary that these compounds be soluble in solvents, and that the compounds have a fixed metal weight. Accordingly, a ligand —C≡C—R with 3 to 10 carbon atoms results in a metal acetylide compound which is readily soluble in solvents and which has a relatively large metal weight, so that such a compound can be adequately used as a metal paste.

Aliphatic hydrocarbon groups which contain oxygen in the form of hydroxy groups may be used as the hydrocarbon group R in cases where this hydrocarbon group contains oxygen. In this case, the group may be linear, or may have side chains. Examples of the ligand —C≡C—R (more concretely, in the form H—C≡C—R) include propyne, 2-propyn-1-ol, 1-butyn-3-ol, 3-methyl-1-butyn-3-ol, 3,3-dimethyl-1-butyne, 1-pentyne, 1-pentyn-3-ol, 4-pentyn-1-ol, 4-pentyn-2-ol, 4-methyl-1-pentyne, 3-methyl-1-pentyn-3-ol, 3,4-dimethyl-1-pentyn-3-ol, 1-hexyne, 1-hexyn-3-ol, 5-hexyn-1-ol, 5-methyl-1-hexyne, 5-methyl-1-hexyn-3-ol, 3,5-dimethyl-1-hexyn-3-ol, 1-heptyne, 1-heptyn-3-ol, 5-heptyn-3-ol, 3,6-dimethyl-1-heptyn-3-ol, 1-octyne and 1-octyn-3-ol, etc.

Furthermore, examples of the hydrocarbon group R include hydrocarbon groups which contain at least a cyclic hydrocarbon containing oxygen in the form of a hydroxy group in cases where the hydrocarbon group R contains oxygen. Such hydrocarbon groups may contain a cyclic hydrocarbon group in the principal chain, or may contain a cyclic hydrocarbon group in a side chain. Furthermore, R as a whole may also be a cyclic hydrocarbon. Here, concrete examples of the ligand —C≡C—R (in the form H—C≡C—R) include 1-ethynyl-1-cyclopropanol, 1-ethynyl-1-cyclobutanol, 1-ethynyl-1-cyclopentanol, 1-ethynyl-1-cyclohexanol, 1-propyne-3-cyclopropanol, 1-propyne-3-cyclobutanol, 1-propyne-3-cyclopentanol, 1-butyne-4-cyclopropanol, 1-butyne-4-cyclobutranol, and 1-pentyne-5-cyclopropanol, etc.

In particular, from the standpoints of ease of obtaining raw materials and ease of manufacture, and from the standpoint of low manufacturing costs, etc., it is advantageous if the ligand —C≡C—R (in the form H—C≡C—R) is 2-propyn-1-ol, 1-butyn-3-ol, 3-methyl-1-butyn-3-ol, 3-methyl-1-pentyn-3-ol, 1-hexyne, 3,5-dimethyl-1-hexyn-3-ol, or 1-ethynyl-1-cyclohexanol.

In the present invention, metal acetylide compounds expressed by the formula M(—C≡C—R)$_n$ (M indicates a metal atom, and n is the valence number of this metal atom) are manufactured by reacting metal salts with acetylene derivatives expressed by the formula H—C≡C—R (R indicates a hydrocarbon group with 1 to 8 carbon atoms which may or may not contain an oxygen atom) so that the metal atom of the metal salt is exchanged with the hydrogen atom of the acetylene derivative. Alternatively, metal acetylide compounds are manufactured by adding a sulfite to a metal salt so that the metal atom of the metal salt is reduced, introducing the acetylene derivative thereinto, and exchanging the reduced metal atom with the hydrogen atom of the acetylene derivative.

In the present invention, the term "metal salt" includes metal acids and salts of metal acids. Concrete examples of such compounds include $HAuCl_4$, $Pd(NO_3)_2$, $KAuCl_4$, $AgNO_3$, $Ru(NO_3)_2$, $Rh(NO_3)_2$ and $Pt(NH_3)_2(NO_3)_2$, etc.

The acetylene derivatives used in the present invention are compounds expressed by the structural formula H—C≡C—R possessing a hydrocarbon group with 1 to 8 carbon atoms which may or may not contain an oxygen atom. Such acetylene derivatives are formed merely by adding a hydrogen atom to the ligand —C≡C—R. Concrete examples for cases in which the compound has an aliphatic hydrocarbon group and case in which the compound has a cyclic hydrocarbon group are the same as in the case of the above-described ligand; accordingly, details are omitted here.

To note again substances which are easily obtainable and easy to manufacture as acetylene derivatives, and which are also inexpensive, such substances include 2-propyn-1-ol, 1-butyn-3-ol, 3-methyl-1-butyn-3-ol, 3-methyl-1-pentyn-3-ol, 1-hexyne, 3,5-dimethyl-1-hexyn-3-ol and 1-ethynyl-1-cyclohexanol, etc.

In cases where the metal atom in the metal salt is not reduced, it is not necessary to use a sulfite; however, a sulfite is used as a reducing agent in cases where the metal atom in the metal salt is reduced. The sulfite used is a solid substance and has the advantage of allowing stoichiometric control of the amount of the reaction when added to an aqueous solution. Unlike sulfur, such a sulfite allows very easy control. Furthermore, in the case of sulfur, there is a danger that the sulfur will be converted into sulfurous acid gas, which is an atmospheric pollutant; sulfites, on the other hand, are safe solid substances and therefore contribute to the cleaning of the environment.

Such sulfites include normal salts and hydrogen salts. Examples of normal sulfites include lithium sulfite, sodium sulfite, potassium sulfite, rubidium sulfite, cesium sulfite, francium sulfite, beryllium sulfite, magnesium sulfite, calcium sulfite, strontium sulfite, barium sulfite and radium sulfite, etc. Furthermore, examples of hydrogensulfites include lithium hydrogensulfite, sodium hydrogensulfite, potassium hydrogensulfite, rubidium hydrogensulfite, cesium hydrogensulfite, francium hydrogensulfite, beryllium hydrogensulfite, magnesium hydrogensulfite, calcium hydrogensulfite, strontium hydrogensulfite, barium hydrogensulfite and radium hydrogensulfite, etc.

In some cases, an exchange-promoting substance is added in order to cause the exchange of the metal atom or reduced metal atom with the hydrogen atom of the acetylene derivative. Such exchange-promoting substances have the function of accelerating the dehydrogenation reaction of the acetylene derivative and causing the bonding of the metal atom in place of the removed hydrogen atom. Examples of such exchange-promoting substances include alkali salts of acetic acid, e. g., sodium acetate, potassium acetate, rubidium acetate, magnesium acetate and calcium acetate, etc. Furthermore, other universally known exchange-promoting substances which focus mainly on the dehydrogenation reaction may also be used.

The reaction formula for the reaction that takes place in cases where the metal atom in the metal salt is not reduced will be shown using palladium as an example. Formula (I) illustrates a case in which palladium nitrate $Pd(NO_3)_2$ is used as a metal salt. Since the metal is not reduced, no sulfite is introduced.

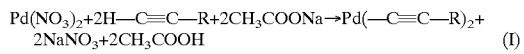

$$Pd(NO_3)_2 + 2H\text{—}C\equiv C\text{—}R + 2CH_3COONa \rightarrow Pd(\text{—}C\equiv C\text{—}R)_2 + 2NaNO_3 + 2CH_3COOH \quad (I)$$

The reaction formulae for reactions that take place in cases where the metal atom in the metal salt is reduced will be shown using gold as an example. Formulae (II) and (III) illustrate cases in which chloroauric acid ($HAuCl_4$) and potassium chloroaurate ($KAuCl_4$) are respectively used as metal salts.

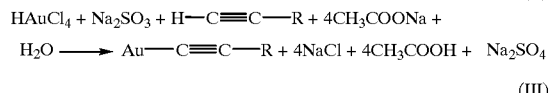

(II)
$$HAuCl_4 + Na_2SO_3 + H\text{—}C\equiv C\text{—}R + 4CH_3COONa + H_2O \longrightarrow Au\text{—}C\equiv C\text{—}R + 4NaCl + 4CH_3COOH + Na_2SO_4$$

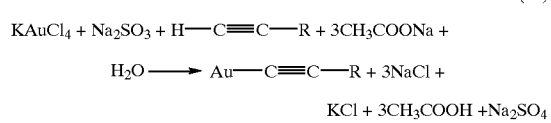

(III)
$$KAuCl_4 + Na_2SO_3 + H\text{—}C\equiv C\text{—}R + 3CH_3COONa + H_2O \longrightarrow Au\text{—}C\equiv C\text{—}R + 3NaCl + KCl + 3CH_3COOH + Na_2SO_4$$

As is clear from the chemical reaction formulae (I) through (III), in cases where the amount of metal salt present is 1 mole, the number of moles of sulfite is given by: (valence number of metal in metal salt–valence number of metal in metal acetylide compound)/2. Furthermore, the number of moles of acetylene derivative is equal to the valence number of the metal in the metal acetylide compound. The reaction can be caused to proceed smoothly by providing amounts of compounds equal to or greater than these theoretical numbers of moles to the reaction system.

The above-described metal salt, sulfite, acetylene derivative and exchange-promoting substance are reacted in a mixed solvent comprising water and a hydrophilic organic solvent. The mixture ratio of the water and hydrophilic organic solvent may be appropriately varied in the range of 20:80~80:20, being preferably in the range of 35:65~65:35 (weight ratio). The metal salt, sulfite and exchange-promoting substance are dissolved in the aqueous component of the mixed solvent, while the acetylene derivative is dissolved in the hydrophilic organic solvent contained in the mixed solvent. The water and hydrophilic organic solvent are uniformly mixed, so that the chemical substances dissolved in the respective phases react with each other, thus producing a metal acetylide compound. From the standpoints of being hydrophilic and having a low boiling point for subsequent evaporation, acetone and alcohols may be cited as desirable examples of hydrophilic organic solvents; however, acetone is the most desirable in that it does not reduce the metal contained in the metal salt.

In the method of the present invention for manufacturing metal acetylide compounds, a metal stabilizing agent may be added in some cases in order to prevent excessive reduction of the metal. For example, when chloroauric acid ($HAuCl_4$) is reduced by means of a sulfite, the gold in this compound may not only be reduced from trivalent to monovalent so that Au—C≡C—R is produced, but may also be excessively reduced so that metallic gold is deposited. Accordingly, if an alkali halide is added as a gold stabilizing agent, the gold will be stabilized in a monovalent state so that a gold acetylide compound can be efficiently produced. Alkali halides such as sodium chloride, potassium chloride and potassium bromide, etc. are suitable as such metal stabilizing agents.

Furthermore, in the method of the present invention for manufacturing metal acetylide compounds, the reaction can be caused to proceed at ordinary temperatures and atmospheric pressure. Accordingly, the method of the present invention is extremely safe, and at the same time, there is no need for any special equipment, so that the overall apparatus is inexpensive.

BEST MODE TO CARRY OUT THE INVENTION PREFERRED EMBODIMENTS OF THE PRESENT INVENTION WILL BE DESCRIBED BELOW

Embodiment 1 [Production of Gold Acetylide Compound]

As a metal salt, 4.2 g of chloroauric acid was added to 50 cc of a mixed solvent in which the ratio of water:acetone was 1:1, and 7.6 g of potassium chloride was added as a metal stabilizing agent; and these ingredients were dissolved under agitation. Next, a solution prepared by dissolving 1.3 g of sodium sulfite in 20 cc of water was added to the solution as a reducing agent. Then, 2.6 g of 3,5-dimethyl-1-hexyn-3-ol used as an acetylene derivative and 7.0 g of sodium acetate trihydrate used as an exchange-promoting substance were added to the mixture, and the resulting mixture was agitated.

A brown sludge-like substance was precipitated in the solvent. It was predicted that this precipitate would be AuC≡C(OH)(CH$_3$)CCH$_2$CH(CH$_3$)$_2$, i. e., the gold acetylide compound AuC$_8$H$_{13}$O in terms of a composition formula. This compound was subjected to differential thermal analysis and atomic absorption analysis, and was thus ascertained to be the predicted gold acetylide compound. Finally, an elemental analysis was performed, and analysis values of 61.0:29.17:3.76:6.07 were obtained with respect to theoretical values of 61.14:29.83:4.07:4.97 for Au:C:H:O. Thus, including error, it was confirmed that this compound was the expected gold acetylide compound.

Embodiment 2 [Production of Platinum Acetylide Compound]

As a metal salt, 1.5 g of dinitirodiamine platinum was added to 50 cc of a mixed solvent in which the ratio of water:acetone was 1:1, and was dissolved under agitation. Next, a solution prepared by dissolving 1.3 g of sodium sulfite in 20 cc of water was added to the solution as a reducing agent. Then, 5.2 g of 3,5-dimethyl-1-hexyn-3-ol used as an acetylene derivative and 7.0 g of sodium acetate trihydrate used as an exchange-promoting substance were added to the mixture, and the resulting mixture was agitated.

A brown sludge-like substance was precipitated in the solvent. It was predicted that this precipitate would be $Pt(C{\equiv}C(OH)(CH_3)CCH_2CH(CH_3)_2)_2$, i. e., the platinum acetylide compound $PtC_{16}H_{26}O_2$ in terms of a composition formula. This compound was subjected to quantitative analysis, differential thermal analysis, atomic absorption analysis and elemental analysis in the same manner as in Embodiment 1, and was thus confirmed to be the predicted platinum acetylide compound.

Embodiment 3 [Production of Palladium Acetylide Compound]

As a metal salt, 2.2 g of palladium nitrate was added to 50 cc of a mixed solvent in which the ratio of water:acetone was 1:1, and 2.2 g of sodium chloride was then added as a metal stabilizing agent; and these ingredients were dissolved under agitation. To this mixture, 7.1 g of 3,5-dimethyl-1-hexyn-3-ol used as an acetylene derivative and 13 g of sodium acetate trihydrate used as an exchange-promoting substance were added, and the resulting mixture was agitated.

A brown sludge-like substance was precipitated in the solvent. It was predicted that this precipitate would be $Pd(C{\equiv}C(OH)(CH_3)CCH_2CH(CH_3)_2)_2$, i. e., the palladium acetylide compound $PdC_{16}H_{26}O_2$ in terms of a composition formula. This compound was subjected to differential thermal analysis, atomic absorption analysis and elemental analysis in the same manner as in Embodiment 1 and was thus confirmed to be the predicted palladium acetylide compound.

The present invention is not limited to the embodiments described above, and various modifications and design alterations which involve no departure from the technical spirit of the present invention are included in the technical scope of the invention.

POSSIBILITES FOR INDUSTRIAL UTILIZATION

As described in detail above, the present invention provides metal acetylide compounds expressed by the general formula $M(-C{\equiv}C-R)_n$ (in the formula, M indicates a metal atom, n indicates the valence number of the metal atom M, and R indicates a hydrocarbon group with 1 to 8 carbon atoms which may or may not contain an oxygen atom). These compounds contain no sulfur or chlorine; accordingly, when these compounds are used as metal pastes, etc., there is no release of sulfurous acid gas or chlorine even if the metal pastes are fired. Thus, these compounds contribute to the cleaning of the environment.

Furthermore, since no sulfurous acid gas is generated in the manufacturing method of the present invention, the present invention can provide a metal acetylide compound manufacturing method which is clean with respect to the environment. Moreover, since a solid sulfite is used in order to reduce the metal in the metal salt, the chemical reaction can easily be controlled in stoichiometric terms.

What is claimed is:

1. Metal acetylide compounds expressed by a general formula $M(-C{\equiv}C-R)_n$, wherein M is a precious metal atom, n indicates a valence number of the precious metal atom M, and R is an aliphatic hydrocarbon group with 1 to 8 carbon atoms which contains oxygen in the form of a hydroxy group in cases where oxygen is contained in the hydrocarbon group.

2. The metal acetylide compounds according to claim 1, wherein the ligand —C≡C—R, in a form of H—C≡C—R, is 2-propyn-1-ol, 1-butyn-3-ol, 3-methyl-1-butyn-3-ol, 3-methyl-1-pentyn-3-ol, 1-hexyne, 3,5-dimethyl-1-hexyn-3-ol or 1-heptyne.

3. A method for manufacturing metal acetylide compounds comprising: adding a sulfite to a metal salt so that a metal atom of the metal salt is reduced, introducing an acetylene derivative expressed by an formula H—C≡C—R (wherein R indicates a hydrocarbon group with 1 to 8 carbon atoms which may or may not contain an oxygen atom) thereinto, exchanging the reduced metal atom and the hydrogen atom of the acetylene derivative, thus producing a metal acetylide compound.

4. The method for manufacturing metal acetylide compounds according to claim 3, wherein a mixed solvent consisting of water and a hydrophilic organic solvent is prepared, the metal salt is dissolved in an aqueous component of the mixed solvent, and the acetylene derivative is dissolved in the hydrophilic organic solvent contained in the mixed solvent.

5. The method for manufacturing metal acetylide compounds according to claim 3, wherein an exchange-promoting substance which causes the metal atom to be exchanged with the hydrogen atom of the acetylene derivative is added.

6. The method for manufacturing metal acetylide compounds according to claim 4, herein an exchange-promoting substance which causes the metal atom to be exchanged with the hydrogen atom of the acetylene derivatives is added.

* * * * *